_United States Patent_ [19]

Leavitt

[11] 4,383,038

[45] May 10, 1983

[54] PROCESS FOR THE PREPARATION OF L-PROLINE BY CULTIVATING ALGAE

[75] Inventor: Richard I. Leavitt, Baton Rouge, La.

[73] Assignee: Ethyl Corporation, Richmond, Va.

[21] Appl. No.: 329,226

[22] Filed: Dec. 10, 1981

[51] Int. Cl.$^3$ .................... C12P 13/24; C12R 1/89
[52] U.S. Cl. .................................. 435/107; 435/946
[58] Field of Search ............................... 435/107, 946

[56] References Cited

U.S. PATENT DOCUMENTS 4,224,409 9/1980 Nakamori et al. .................. 435/107

FOREIGN PATENT DOCUMENTS 1132036 10/1968 United Kingdom.

OTHER PUBLICATIONS

Aust. J. Plant Physiology, 1979, vol. 6, pp. 69–79.
Limnol. Oceanographer, vol. 10, pp. 192–206 (1965).

_Primary Examiner_—Lionel M. Shapiro
_Attorney, Agent, or Firm_—Donald L. Johnson; John F. Sieberth; Willard G. Montgomery

[57] ABSTRACT

A process for producing L-proline by cultivating Chlorella sp. 580 algae under high-intensity illumination in an aqueous growth medium containing a high concentration of sodium chloride (at least 1 M in the final stage of cultivation), providing an adequate supply of carbon, in a depth not exceeding approximately 20 cm of the aqueous medium, until algae of high L-proline content are obtained, harvesting the algae and thereafter recovering L-proline from the algae.

18 Claims, No Drawings

PROCESS FOR THE PREPARATION OF L-PROLINE BY CULTIVATING ALGAE

BACKGROUND OF THE INVENTION

This invention relates to a process for producing L-proline. More particularly, it relates to a process for the production of L-proline in high yields by cultivation and work-up of a certain type of algae, specifically Chlorella sp. 580. Conditions of cultivation and work-up are defined.

L-proline is a useful amino acid which is used as a medicine and in other applications. In the past, L-proline has been produced mainly by isolation from hydrolysates of proteins or gelatin or by organic synthesis. However, the yield of product obtained by these methods is very low, and the procedures involved are complicated. As a result, L-proline is one of the most expensive amino acids. Therefore, the development of a process for the mass production of L-proline using inexpensive starting materials would be highly desirable.

The fact that L-proline is contained in algae of the genus Chlorella is known. Further, it is known that L-proline is produced by the Chlorella algae in response to the environment in which it is grown, i.e. the sodium chloride content of the growth medium. The relationship between L-proline cell accumulation in *Chlorella emersonii* and sodium chloride content of the environment external of the cell has been described in *AUST. J. Plant Physiology* (1979) 6,69-79 in which it was reported that in the emersonii species of Chlorella, L-proline production within the cell generally increases as the sodium chloride concentration is increased in the environment external to the cell. However, it appears that only small amounts of L-proline are produced within *Chlorella emersonii* and, at sodium chloride concentrations higher than 335 mM, the cells plasmolyze.

The fact that Chlorella sp. 580 excrete proline also is known as reported in *Limnol. Oceanographer* (1965) 10:192-206. However, the excretion levels reported therein also are small.

Methods for producing L-proline by fermentation also are known. For example, British Pat. No. 1,132,036 discloses that L-proline can be produced from mutant strains of *Micrococcus glutamicus* by fermentation. Also, U.S. Pat. No. 4,224,409 discloses that L-proline can be obtained by culturing a mutant of the genus Brevibacterium, Corynebacterium or Microbacterium. L-proline production by fermentation, however, is somewhat expensive since the sources of carbon for use in the fermentation medium include carbon sources other than $CO_2$, such as, for example, pentoses, hexoses, disaccharides, or the like.

Thus, even though it is known that L-proline can be produced both intracellularly and extracellularly by the genus Chlorella, insofar as Applicant is aware, nothing has been reported in the literature with respect to the identification of a specific species of Chlorella and a specific method of cultivating said specific organism such that L-proline can be produced intracellularly within the organism in amounts high enough to be considered sufficient to form the basis for an industrial process.

SUMMARY OF THE INVENTION

In accordance with the present invention, applicant has isolated and cultivated a species of algae as a pure algal culture which can be used for the production of L-proline in high quantities. Applicant has achieved this result by culturing Chlorella sp. 580 algae under high-intensity illumination in an aqueous growth medium containing an assimilable carbon source, assimilable nitrogen sources, inorganic salts and, if required, small amounts of organic nutrients such as vitamins, or the like, required for the growth of the algae and a high concentration of sodium chloride of at least 1 M in the final stage of the cultivation under an aerobic condition until algae of high L-proline content are obtained. The L-proline containing algae are then harvested and the L-proline thus produced is recovered.

DESCRIPTION OF THE PREFERRED EMBODIMENT

In a preferred embodiment of the present invention, there is provided a process for the production of L-proline which comprises cultivating Chlorella sp. 580 algae under high-intensity illumination in an aqueous growth medium containing an amount sufficient of nutrients including nitrogen to effect growth of the algae and a high concentration of sodium chloride which reaches at least 1 M in the final stage of cultivation under an aerobic condition, providing an adequate supply of carbon, in a depth not exceeding approximately 20 cm of the aqueous medium, until algae of high L-proline content are obtained, harvesting the algae and recovering from same the L-proline thus produced.

The algae used in the process of the invention are designated Chlorella sp. 580 which belong to the Class of Chlorellaceae, Order of chlorophyta. The algae are unicellular, non-motile, non-nitrogen fixing cells, which are round to oval in shape. The cells are approximately 5 to 10 $\mu$m in diameter and have a rigid cell wall. Under optimum conditions of cultivations, the L-proline content of each cell can be increased to approximately 15% to 35% of the cell weight or from about 150 mg to about 350 mg per gram dry weight of algae.

Cultivation is under an adequately high intensity of illumination and can be carried out outdoors in sunlight, or artificial light may be used if desired. If artificial light is used, the intensity of illumination should be at least 200 f.c. to 1000 f.c., and preferably 300 f.c. When cultivated outdoors, the depth of the water should not exceed about 20 cm, and the optimum depth is from about 7.5 cm to about 15 cm.

The cultivation is carried out either on an artificial medium or on sea-water adjusted so as to contain the required nutrients and salt concentrations. The aqueous culture medium employed in the present invention contains an assimilable carbon source, preferably $CO_2$, assimilable nitrogen sources, conventional inorganic salts, such as, for example, the phosphates, sulfates, nitrates, chlorides and other salts of potassium sodium, calcium, magnesium, iron, zinc, manganese, cobalt, copper, etc., and if necessary, minor organic nutrients, such as, vitamins, or the like. Such nutrients are well known in the art.

As a nitrogen source, various kinds of inorganic or organic salts or compounds such as potassium nitrate, sodium nitrate, ammonia, ammonium sulfate, ammonium chloride, ammonium nitrate, or ammonium carbonate may be used. Mixtures of these substances may also be used.

As indicated above, it is possible to use sea-water augmented by the addition of various nutrient constituents aforedisclosed or concentrated by partial evaporation and addition of aforedisclosed constituents. If supplemented sea-water is used, it should have a sodium chloride content sufficient for the production of L-proline in high amounts, supplemented with a nitrogen source such as NaNO$_3$, 50 mg/l to 1.0 g/l, and phosphate source such as K$_2$HPO$_4$, 15 mg/l to 300 mg/l.

There must be provided a suitable and adequate source of carbon. A 5% CO$_2$ enriched atmosphere can be used if desired.

Also, biotin and vitamins such as thiamine and cyanocobalamine may be used.

Cultivation is carried out under an aerobic condition, such as aerobic shaking of the culture or stirring of a submerged culture with introduction of air thereinto, at a temperature of from about 10° C. to about 40° C., preferably 25° C. to about 35° C., and at a pH of about 7.0 to about 9.0. An optimum pH is about 8.0. The pH is advantageously adjusted by adding quantities of CO$_2$ and mineral acids such as hydrochloric acid or nitric acid as required.

The production of high quantities of L-proline in Chlorella sp. 580 algae is brought about by increasing the salinity of its growth medium. That is, the algae are cultured for a period of time in a growth medium containing a low concentration of sodium chloride such as, for example, from about 0.25 to about 0.5 M NaCl, preferably about 0.5 M NaCl, and then the algae are stressed by increasing the salinity of the medium whereby excess amounts of L-proline are produced within the algae cells. Normally, the addition of sodium chloride to the medium inhibits cell growth and hence reduces L-proline production as demonstrated in Example 1 below. However, applicant has found that the cells can be salt "adapted" to grow in the presence of relatively high concentrations of sodium chloride by first culturing the algae in a medium containing a relatively low concentration of sodium chloride and thereafter increasing the sodium chloride concentration in the medium whereby excess L-proline production is stimulated within the cells.

Thus the production of L-proline can be broken down into two phases. In the first phase, or the growth phase, the algae are added to a suitable growth medium (supplemented tap or sea-water) at low density and allowed to divide and increase their cell number and mass for a period of time, normally between three to twenty-one days, until they have reached a cell density of from about 250 to about 5000 mg/l based on dry cell weight. The inoculation volume is normally between 5 and 10 volume percent of the uninoculated culture. The early culture should be grown in media which have been previously sterilized. In general, the first 20% of the inoculation chain should be accomplished using sterile media. Upon reaching the aforementioned cell density, the algae are then transferred promptly to a culture medium having a higher concentration of sodium chloride and the cells are then made proline productive by continued incubation without growth for an additional period of time of from 6 to 80 hours, typically 16 hours. This is the second phase, or proline production phase, of the process. In lieu of transferring the algae from one medium having a lower sodium chloride concentration to a second and separate medium containing a higher sodium chloride concentration, the sodium chloride content of the original growth medium can simply be increased to a higher concentration at the end of the growth phase. For optimal growth and proline production, Applicant has found that growth in the presence of approximately 0.5 M sodium chloride followed by proline production in the presence of 1.0 M sodium chloride to yield the highest level of proline production. Although the sodium chloride concentration can be increased above 1 M in the final stage of cultivation, Applicant has found thus far no significant increase in L-proline to cell ratios when the sodium chloride concentration is increased beyond 1 molar. Thus, in a more specific embodiment of the present invention, there is provided a process for the production of L-proline which comprises cultivating Chlorella sp. 580 algae under high-intensity illumination in an aqueous growth medium containing an amount sufficient of nutrients including nitrogen to effect growth of the algae and a sodium chloride concentration of up to 0.5 M under an aerobic condition, providing an adequate supply of carbon, in a depth not exceeding approximately 20 cm of the aqueous medium, for a period of time sufficient for the algae to attain a cell density of up to at least 5 grams/l and thereafter increasing the sodium chloride concentration in the medium to 1 molar and continuing cultivating the algae until algae of high L-proline content are obtained, harvesting the algae and recovering from same the L-proline thus produced.

Cells grown in the absence of sodium chloride do not become as proline productive as cells grown in the presence of sodium chloride regardless of the time allowed for the proline production cycle.

After completion of culturing and proline production, the cells are harvested (separated from the culture liquor) and the proline is recovered from the cells.

Harvesting can be accomplished by conventional methods such as sedimentation, filtration or centrifugation. Optionally, a flocculant may be added to the aqueous culture to concentrate the cells into a singular mass prior to settling or implementation of any of the other aforementioned harvesting techniques. Alumina has been found to be a particularly effective flocculant. Suitable sources of Al$^{+3}$ flocculant are aluminum salts such as Al(NO$_3$)$_3$.9H$_2$O; Al$_2$(SO$_4$)$_3$.10H$_2$O; AlNH$_4$(SO$_4$)$_2$.10H$_2$O and Al$_2$(SO$_4$)$_3$.18H$_2$O. In general, the addition of from about 5 to about 100 ppm of Al$^{+3}$ to a typical cell suspension is sufficient to bring about a 10 fold to 100 fold increase in density (g/l) of the cells. Flocculation is generally complete within 1 to 5 minutes, and essentially complete clarification of the culture liquor is achieved within 1 to 24 hours.

After harvesting, the cells are suspended in water and heated to above 80° C., typically 100° C., for a period of time of up to about 1 hour, whereupon the L-proline accumulated within the cells is released from the cells into the water. L-proline is then recovered from the water phase by any known methods such as by using ion-exchange resin, acid or alcohol extraction.

Optionally, L-proline can be recovered simply by harvesting the cells as described above to remove the culture liquor therefrom and subsequently reducing the molarity of the sodium chloride concentration originally added in order to achieve maximum proline production by suspending the cells in fresh water in an amount sufficient to cause release of the proline into the water phase. Cell concentrates made proline-rich by the addition of sodium chloride can be made to release up to 100% of their proline by simple dilution of the sodium chloride solution with fresh water. Partial release occurs when the salt concentration is reduced below 0.3 M and generally complete release occurs at dilutions below 0.14 M sodium chloride. Dilution recovery is carried out at room temperature.

The proline is recovered and purified by conventional methods such as ion-exchange chromatography, thin layer chromatography, gas chromatography and obtained in crystalline form.

Typically, amino acids other than L-proline are present in the extract or water phase following proline release from the cells. The total amount of non-proline amino acids can range up to as high as 10 weight percent with alanine typically being present in the highest amounts.

The following examples are given merely as illustrative of the present invention and are not to be considered as limiting.

EXAMPLE 1

This example demonstrates that as the sodium chloride concentration in a culture medium containing Chlorella sp. 580 is increased, cell growth is progressively inhibited.

An aqueous medium (deionized water) was prepared containing 0.017 g/l $K_2HPO_4$, 0.340 g/l $NaNO_3$, 0.100 g/l $KNO_3$, 0.043 g/l $NaHCO_3$, 5.95 g/l $MgSO_4.7H_2O$, 4.10 g/l $MgCl_2$ 1.47 g/l $CaCl_2$, 0.00024 g/l $FeCl_3$, 0.00011 g/l $ZnCl_2$ 0.0114 g/l ethylenediamine tetraaceticacid, 0.00104 g/l $H_3BO_3$, 0.00126 g/l $MnCl_2$, 0.00000473 g/l $CoCl_2$, 0.000000266 g/l $CuCl_2$, 0.0002 g/l thiamine-HCL, 0.00001 g/l biotin and 0.000001 g/l cyanocobalamin. A 20 ml aliquot of the aqueous medium was placed into five separate 125 ml flasks. In the first flask, no sodium chloride was added to the medium. In the second, third, fourth, and fifth flasks sodium chloride was added to the medium so that the medium in flask No. 2 contained 0.25 M NaCl, the medium in flask No. 3 contained 0.5 M NaCl, the medium in flask No. 4 contained 1 M NaCl and the medium in flask No. 5 contained 2 M NaCl. Each medium was then inoculated with Chlorella sp. 580 (50 mg/l) and cultured at approximately 30° C. for 72 hours in a 5% $CO_2$ enriched atmosphere with shaking under a bank of fluorescent lights at an average luminescence of 300 candle foot power. The lights were located approximately 30 cm from the surface of the culture. The pH was maintained at between 7.0 and 9.0 by adding $CO_2$. After the cultivation, the cells were harvested by sedimentation. The culture liquors were decanted from the flasks and the cell weights determined. Loss in cell weight indicated growth inhibition. The results are set forth in Table 1 below.

TABLE 1

| Culture No. | NaCl (M) In Culture Medium | Cell Weight After Cultivation (mg/l) | % Growth Inhibition |
|---|---|---|---|
| 1 | 0 | 444 | 0 |
| 2 | 0.25 | 296 | 33 |
| 3 | 0.50 | 222 | 50 |
| 4 | 1.00 | 107 | 76 |
| 5 | 2.00 | 33 | 93 |

As demonstrated in the table, as the molarity of the NaCl is increased in the culture medium, growth of Chlorella sp. 580 cells progressively decreases. At a NaCl concentration of 0.5 M, a 50% inhibition in cell growth was observed. When the NaCl concentration in the medium was 2 M, a 93% inhibition in cell growth prevailed.

EXAMPLE 2

This example demonstrates that Chlorella sp. 580 can be salt adapted to grow in the presence of relatively high concentrations of sodium chloride.

An aqueous medium was prepared as described in Example 1. A 20 ml aliquot of the medium was placed in a 125 ml flask. A second 20 ml aliquot of medium was placed in a separate 125 ml flask and 1 M NaCl was added to the medium. Each medium was then inoculated with Chlorella sp. 580 (50 mg/l) and cultivated under the same conditions and for the same period of time as set forth in Example 1.

After cultivation, the cells were harvested by sedimentation and transferred (subcultured) into eight separate media identical in composition to the original medium in which the cells were cultured except that each medium contained different concentrations of NaCl as indicated in Table 2 below. Each of the eight media were inoculated with 50 mg/l of the algae. Four of the media were inoculated with NaCl "adapted cells", i.e. those originally grown in medium containing 1 M NaCl, and four were inoculated with NaCl "unadapted cells", i.e. those originally grown in medium containing no sodium chloride. The cells were then cultivated under the same condition and for the same period of time as the original cultures. After cultivation, the cells were harvested by sedimentation, the culture liquors were decanted from the cells and the cell weight determined. The results from the second cultivations are shown in Table 2 below.

TABLE 2

| | Inocula (unadapted cells) | | Inocula (adapted cells) | |
|---|---|---|---|---|
| NaCl (M) in 2nd Culture Medium | Cell Weight after 72 hrs Growth (g/l) | % Growth Inhibition | Cell Weight after 72 hrs Growth (g/l) | % Growth Inhibit |
| 0 | 1.30 | — | 1.30 | — |
| 0.5 | 1.07 | 18 | 1.14 | 12 |
| 1.0 | 0.592 | 56 | 0.815 | 37 |
| 1.5 | 0.085 | 93 | 0.333 | 74 |

The results in Table 2 demonstrate that Chlorella sp. 580 can be salt adapted to grow in the presence of relatively high concentrations of NaCl. As shown in the table, those cells previously cultivated in a NaCl containing medium and then subsequently subcultured in media also containing NaCl exhibited a decrease in growth inhibition when contrasted to those cells which were originally cultivated in a non-NaCl containing medium and then subcultured in a NaCl containing medium.

EXAMPLE 3

This example demonstrates the production of L-proline by Chlorella sp. 580 when the algae were grown in the presence of either 0.0 M, 0.25 M, 0.5 M or 1 M NaCl and then made proline productive by the addition of NaCl (1 M) to the culture medium.

An aqueous culture medium was prepared as described in Example 1. A 20 ml aliquot of the medium was then placed into four separate 125 ml flasks. The medium in the first flask contained no sodium chloride. Sodium chloride was added to the media in the second, third and fourth flasks such that the medium in flask No. 2 contained 0.25 M NaCl, the medium in flask No. 3 contained 0.5 M NaCl, and the medium in flask No. 4 contained 1 M NaCl. Each medium was then inoculated with Chlorella sp. 580 (50 mg/l) and cultivated at approximately 30° C. for 72 hours in a 5% $CO_2$ enriched atmosphere with shaking under a bank of fluorescent lights at an average luminescence of 300 candle foot power. The lights were located approximately 30 cm from the surface of the cultures, the pH was maintained at approximately 8.0 by adding $CO_2$ on demand.

At the end of 72 hours, an amount of sodium chloride sufficient to bring the level of the sodium chloride concentrations in the culture medium up to 1 M NaCl was added to each medium. The cultures were then shaken for an additional 16 hours to achieve proline enrichment. At the end of the 16 hours, the cells were harvested by centrifugation from their respective cultures and their contents examined for the presence of L-proline. This was accomplished by decanting the culture liquor from the cells after centrifugation and then suspending the cells in fresh water and heating at 100° C. for approximately 20 minutes to extract the proline from the cells into the aqueous phase. The amount of proline produced by the cells was determined by thin layer of chromatography. The results are set forth in Table 3 below.

TABLE 3

| Culture No. | Molarity of NaCl During Growth | Molarity of NaCl After Growth | mg Proline/ mg Cell |
|---|---|---|---|
| 1 | 0 | 1.0 | 0.11 |
| 2 | 0.25 | 1.0 | 0.15 |
| 3 | 0.50 | 1.0 | 0.20 |
| 4 | 1.0 | 1.0 | 0.275 |

As demonstrated in the Table, L-proline production increased in response to the addition of NaCl to the growth medium. Cells grown in the absence of sodium chloride (culture No. 1) did not become as proline productive as cells grown in the presence of sodium chloride. Those cells grown in salt containing media exhibited increased levels of L-proline production when the salt concentrations of the media were increased to 1 molar.

I claim:

1. A process for the production of L-proline, which comprises cultivating Chlorella sp. 580 algae under high-intensity illumination in an aqueous growth medium containing an amount sufficient of nutrients including nitrogen to effect growth of the algae and a high concentration of sodium chloride which reaches at least 1 M in the final stage of cultivation under an aerobic condition, providing an adequate supply of carbon, in a depth not exceeding approximately 20 cm of the aqueous medium, until algae of high L-proline content are obtained, harvesting the algae and recovering from same the L-proline thus produced.

2. A process according to claim 1 wherein said growth medium is an artificial aqueous growth medium containing:
0.017 g/l $K_2HPO_4$, 0.340 g/l $NaNO_3$, 0.100 g/l $KNO_3$, 0.043 g/l $NaHCO_3$, 5.95 g/l $MgSO_4.7H_2O$, 4.10 g/l $MgCl_2$ 1.47 g/l $CaCl_2$, 0.00024 g/l $FeCl_3$, 0.00011 g/l $ZnCl_2$, 0.0114 g/l ethylenediamine tetraacetic acid, 0.00104 g/l $H_3BO_3$, 0.00126 g/l $MnCl_2$, 0.00000473 g/l $CoCl_2$, 0.000000266 g/l $CuCl_2$, 0.0002 g/l thiamine-HCL, 0.000001 g/l biotin and 0.000001 g/l cyanocobalamin.

3. A process according to claim 1, wherein the cultivation is carried out in sunlight.

4. A process according to claim 1, wherein the cultivation is carried out in the presence of artificial light.

5. A process according to claim 4, wherein the intensity of illumination is between 200 f.c. and 1000 f.c.

6. A process according to claim 1, wherein the carbon is supplied in the form of $CO_2$ at a pH of from 7.0 to 9.0.

7. A process according to claim 1, wherein cultivation is carried out at a temperature of from between about 10° C. and about 40° C.

8. A process according to claim 1, wherein algae are harvested by sedimentation.

9. A process for the production of L-proline which comprises cultivating Chlorella sp. 580 algae under high-intensity illumination in an aqueous growth medium containing an amount sufficient of nutrients including nitrogen to effect growth of the algae in a sodium chloride concentration of up to 0.5 M under an aerobic condition, providing an adequate supply of carbon in a depth not exceeding approximately 20 cm of the aqueous medium for a period of time sufficient for the algae to obtain a cell density of up to at least 5 g/l and thereafter increasing the sodium chloride concentration in the medium to 1 molar and continuing cultivating the algae until algae of high L-proline content are obtained, harvesting the algae and recovering from same the L-proline thus produced.

10. A process according to claim 9, wherein said aqueous growth medium is an artificial growth medium containing:
0.017 g/l $K_2HPO_4$, 0.340 g/l $NaNO_3$, 0.100 g/l $KNO_3$, 0.043 g/l $NaHCO_3$, 5.95 g/l $MgSO_4.7H_2O$, 4.10 g/l $MgCl_2$ 1.47 g/l $CaCl_2$, 0.00024 g/l $FeCl_3$, 0.00011 g/l $ZnCl_2$, 0.0114 g/l ethylenediamine tetraacetic acid 0.00104 rg/l $H_3BO_3$, 0.00126 g/l $MnCl_2$, 0.00000473 g/l $CoCl_2$, 0.000000266 g/l $CuCl_2$, 0.002 g/l thiamine-HCl, 0.000001 g/l biotin and 0.000001 g/l cyanocobalamin.

11. A process according to claim 9, wherein the cultivation is carried out in sunlight.

12. A process according to claim 9, wherein the cultivation is carried out in the presence of artificial light.

13. A process according to claim 12, wherein the intensity of illumination is between about 200 f.c. and 1000 f.c.

14. A process according to claim 9, wherein the carbon is supplied in the form of $CO_2$ at a pH up to 7.0 to 9.0.

15. A process according to claim 9, wherein said algae are cultivated in the presence of a sodium chloride concentration of up to 0.5 M for a period of time of from 3 to 21 days.

16. A process according to claim 9, wherein said algae are cultivated in the presence of a sodium chloride concentration of 1 M for a period of time of from 6 to 80 hours.

17. A process according to claim 9, wherein cultivation is carried out at a temperature of from about 10° C. to about 40° C.

18. A process according to claim 9, wherein the algae are harvested by sedimentation.

* * * * *

UNITED STATES PATENT AND TRADEMARK OFFICE
CERTIFICATE OF CORRECTION

PATENT NO. : 4,383,038
DATED : May 10, 1983
INVENTOR(S) : Richard I. Leavitt

It is certified that error appears in the above—identified patent and that said Letters Patent is hereby corrected as shown below:

Column 2, line 55, reads "potassium sodium", and should read
-- potassium, sodium --.

Column 2, line 56, reads "zinc manganese", and should read
-- zinc, manganese --.

Column 3, line 23, reads "saltinity", and should read
-- salinity --.

Column 8, line 38, reads "rg/l $H_3BO_3$,", and should read
-- g/l $H_3BO_3$ --.

Column 5, line 26, reads "$ZnCl_2$0.0114", and should read
-- ZnCl, 0.0114 --.

Column 5, line 29, reads "HCl, 0.00001 g/l", and should read
-- HCl, 0.000001 g/l --.

Signed and Sealed this

Fifteenth Day of November 1983

[SEAL]

Attest:

GERALD J. MOSSINGHOFF

Attesting Officer

Commissioner of Patents and Trademarks